United States Patent [19]

Krimmer et al.

[11] Patent Number: 4,952,706

[45] Date of Patent: Aug. 28, 1990

[54] DERIVATIVES OF 2-PYRROLIDONE-5-CARBOXYLIC ACID AND METHOD OF OBTAINING THEM

[75] Inventors: Hans-Peter Krimmer, Frankfurt; Karlheinz Drauz, Freigericht, both of Fed. Rep. of Germany

[73] Assignee: Degussa Aktiengesellschaft, Frankfurt am Main, Fed. Rep. of Germany

[21] Appl. No.: 417,089

[22] Filed: Oct. 4, 1989

[30] Foreign Application Priority Data

Oct. 6, 1988 [DE] Fed. Rep. of Germany ....... 3833972

[51] Int. Cl.$^5$ .......................................... C07D 207/12
[52] U.S. Cl. .................................................. 548/534
[58] Field of Search ........................................ 548/534

[56] References Cited

U.S. PATENT DOCUMENTS

| 2,806,855 | 9/1957 | Hoglan | 548/534 |
|---|---|---|---|
| 2,984,684 | 5/1961 | Fike | 548/534 X |
| 3,153,049 | 10/1964 | Melis et al. | 548/534 |
| 3,185,703 | 5/1965 | Kageyama et al. | 548/534 |
| 3,235,563 | 2/1966 | Noyori | 548/534 |
| 3,952,011 | 4/1976 | Dazai | 548/534 |
| 4,097,490 | 6/1978 | Reinhold | 548/534 |

FOREIGN PATENT DOCUMENTS

| 38-17678 | 9/1963 | Japan | 548/534 |
|---|---|---|---|
| 42-18606 | 9/1967 | Japan | 548/534 |
| 110559 | 9/1976 | Japan | 548/534 |

*Primary Examiner*—Joseph Paul Brust
*Attorney, Agent, or Firm*—Cushman, Darby & Cushman

[57] ABSTRACT

The new, crystalline trihydrates of sodium L- and D-2-pyrrolidone-5-carboxylate. These trihydrates can be obtained by adjusting the concentration and the temperature in an aqueous solution of sodium L- or D-2-pyrrolidone-5-carboxlate in such a manner that the solubility of the desired trihydrate is exceeded.

3 Claims, No Drawings

DERIVATIVES OF 2-PYRROLIDONE-5-CARBOXYLIC ACID AND METHOD OF OBTAINING THEM

The present invention relates to the two enantiomers of the pure, crystalline trihydrate of sodium-2-pyrrolidone-5-carboxylate of the formula:

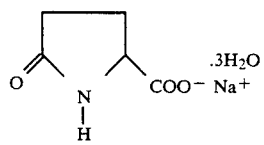

and a method of obtaining them.

BACKGROUND OF THE INVENTION

Sodium-2-pyrrolidone-5-carboxylate, also called sodium pyroglutamate for short, is known in the L and D forms and also as a racemate. However, the crystalline trihydrates of sodium L- and D-pyroglutamate are new compounds which have not been previously described in the literature.

These compounds have proven to be suitable for the production of pesticides, drugs, cosmetics and especially of moisture-containing solutions, mixtures, emulsions, suspensions and the like.

SUMMARY OF THE INVENTION

The present invention provides new trihydrates of sodium L- and D- 2-pyrrolidone-5-carboxylate.

The present invention also provides a method for making trihydrates of sodium L- and D- 2-pyrrolidone-5-carboxylate. In that method, an aqueous solution is formed which contains the enantiomer of sodium L- or D-2-pyrrolidone-5-carboxylate whose trihydrate is desired, either alone or in a mixture of that enantiomer and the other enatiomer which mixture contains at the most 15 mole % of the other enantiomer. The total concentration of both enatiomers, i.e. the concentration of the enantiomer whose trihydrate is desired and the other enantiomer is in the range between 40 and 73.65% by weight and the temperature is in the range between $-20°$ C. and $+42°$ C. The concentrations of the enantiomers in this solution are coordinated in such a manner with one another and with the temperature that the solubility of the desired trihydrate is exceeded.

Since the solubility is a function both of the concentration and also of the temperature, the crystallization can be achieved by removing a part of the water from a diluted, aqueous solution, thus resulting in a higher concentration. The removal of the water can be achieved by elevating the temperature of the solution or by applying a vacuum or, best of all, by means of a combination of these two methods.

It is also possible to bring about the crystallization by lowering the temperature of the solution.

Since the solubility of the desired trihydrate drops as the temperature falls, a minimum concentration of sodium L- or D-pyroglutamate is necessary for crystallization at every temperature. In the following, the indications of concentration signify percents by weight.

Thus, approximately 20% of the entire amount crystallizes out as trihydrate at 20° C. from a 55% aqueous solution of sodium L-pyroglutamate. At the same temperature, at a concentration of 60%, over 75% of the total amount is obtained as crystalline trihydrate. The upper concentration limit is 73.65%, since the water content of the trihydrate itself is 26.35%. Thus, the desired trihydrate is obtained practically quantitatively in the crystallization of solutions which contain more than 70% sodium L- or D-pyroglutamate.

If the temperature of the solution is reduced, lower concentrations suffice to bring about a crystallization. Thus, crystalline sodium L- or D-pyroglutamate trihydrate can be obtained at 0° C. from a 48% solution. A 40% solution crystallizes at $-20°$ C. Lower temperatures are not to be recommended since there is a risk of some of the water freezing. The upper temperature limit is 42° C., since this is the melting point of crystalline sodium L- or D-pyroglutamate trihydrate.

During the crystallization of a solution containing a mixture of sodium L- and D-pyroglutamate, only the enantiomer crystallizes which is present in the higher concentration. However, if the portion of the enantiomer present in a lesser concentration is more than 15 mole %, then no crystallization of the other enantiomer takes place.

The method of the invention can therefore also be used in mixtures of sodium L-and D-pyroglutamate containing one of the two enantiomers at more than 85 mole % to separate the latter from said mixtures in an optically pure form.

It is basically immaterial in the method of the invention how the aqueous solutions of sodium L- or D-pyroglutamate are prepared. One possibility is to neutralize L- or D-pyroglutamic acid in aqueous solution with sodium hydroxide solution. Another possibility is to dissolve solid sodium L- or D-pyroglutamate, which can be obtained by melting sodium L- or D-glutamate monohydrate, in water.

DETAILED DESCRIPTION OF PREFERRED EMBODIMENTS

The invention is explained in more detail in the following examples:

EXAMPLE 1:

129.1 g (1 mole) L-pyroglutamic acid were suspended in 200 ml water. 250 ml (1 mole) 4N sodium hydroxide solution were added in drop-by-drop with water cooling. The L-pyroglutamic acid went completely into solution thereby as sodium salt. The pH was 8.3. 320 ml water were distilled off in a rotary evaporator at a bath temperature of 45° C. and a pressure of 25 mbar. The water content of the residual solution was 39% (titration according to Karl-Fischer). During cooling to 20° C., 158 g (77% of theory) colorless sodium L-2-pyrrolidone-5-carboxylate trihydrate precipitated as a coarse, crystalline precipitation with a melting point of 42° C.

$C_5H_6NNaO_3.3H_2O(205.14)$

| | | | | |
|---|---|---|---|---|
| Calculated: | C 29.26% | H 5.85% | N 6.82% | H$_2$O 26.35% |
| Observed: | C 29.44% | H 5.98% | N 6.76% | H$_2$O 26.44% |

$[\alpha]_D^{20}$: $-18.68°$ (c=4, H$_2$O).

$^1$H—NMR (d$^6$—DMSO): τ32 1.80–2.15 (m; 4H, CH$_2$—CH$_2$), 3.51 (s; 6H, 3 H$_2$O), 3.69 (t; 1H, CH), 7.66 (s; 1H, NH).

IR (KBr): 3700–2800 (wide, s), 1678 (s), 1593 (s), 1412 (m), 1300 (m), 1155 (w), 1104 (w), 1043 (w), 1009 (w), 723 (w) cm$^{-1}$.

EXAMPLE 2:

A 50% solution of sodium L-pyroglutamate was prepared in water in a manner analogous to Example 1. No crystalline precipitation formed at 20° C. During cooling to 0° C., 52% of theory crystalline sodium L-pyroglutamate trihydrate was obtained.

EXAMPLE 3

A 40% solution of sodium L-pyroglutamate was prepared in water in a manner analogous to Example 1. During cooling to −20° C., 31% of theory crystalline sodium L-pyroglutamate trihydrate was obtained.

EXAMPLE 4:

A 60% solution of sodium D-pyroglutamate was prepared in water in a manner analogous to Example 1. D-pyroglutamic acid was added as initial product. During cooling to 20° C., 74% of theory colorless, crystalline sodium D-2-pyrrolidone-5-carboxylate trihydrate was obtained which had a melting point of 42° C.

$[\alpha]_D^{20}$: +18.74° (c=4, H$_2$O).

EXAMPLE 5:

100 g (0.66 mole) sodium L-pyroglutamate which had been obtained by melting sodium L-glutamate monohydrate, were dissolved in 43 ml water at 50° C. The 70% solution was cooled to 20° C. 130 g (96% of theory) sodium L-pyroglutamate trihydrate precipitated as colorless crystals.

EXAMPLE 6:

11.62 g (0.09 mole) L-pyroglutamic acid and 1.29 g (0.01 mole) D-pyroglutamic acid were suspended in 20 ml water. 25 ml (0.1 mole) 4N sodium hydroxide solution was added drop-by-drop with water cooling. 32 ml water were distilled off in a rotary evaporator. The residual solution was cooled to 20° C. 12.3 g (67% of theory) colorless sodium L-pyroglutamate trihydrate with a melting point of 42° C. precipitated.

$[\alpha]_D^{20}$: −18.55° (c=4, H$_2$O).

For the exact determination of the enantiomeric purity, a specimen was analyzed by means of a chiral GC column after derivatization, first with methanol/hydrogen chloride, and subsequently with trifluoroacetic acid anhydride (Chirasil-Val; l=10 m; solvent: dichloromethane/diethyl ketone (1: 1); T=110° C.). After comparison with the reference substances L-pyroglutamic acid and D-pyroglutamic acid, the specimen consisted of 99.8% L and 0.2% D enantiomer.

EXAMPLE 7:

A mixture of 85 mole % sodium L-pyroglutamate and 15 mole % sodium D-pyroglutamate crystallized in a manner analogous to Example 6. 12% of theory sodium L-pyroglutamate trihydrate was obtained at a concentration of 60% in the solution during cooling to −10° C.

$[\alpha]_D^{20}$: −18.3° (c=4, H$_2$O).

What is claimed is:

1. Sodium L-2-pyrrolidone-5-carboxylate trihydrate.
2. Sodium D-2-pyrrolidone-5-carboxylate trihydrate.
3. A method of obtaining sodium L- or D-2-pyrrolidone-5-carboxylate trihydrate comprising forming an aqueous solution of a member of the group consisting of sodium L-2-pyrrolidone-5-carboxylate, sodium D-2-pyrrolidone-5-carboxylate and mixtures of sodium D-2-pyrrolidone-5-carboxylate and sodium L-2-pyrrolidone-5-carboxylate containing at the most 15 mole % of the enantiomer whose trihydrate is not to be obtained, and adjusting (a) the concentration of the solution in a range between 40 and 73.65% by weight of said member of the group consisting of sodium L-2-pyrrolidone-5-carboxylate, sodium D-2-pyrrolidone-carboxylate and mixtures of sodium D-2-pyrrolidone-5-carboxylate and sodium L-2-pyrrolidone-5-carboxylate and (b) the temperature in a range between −20° C. and +42° C. so that at the resulting concentration and temperature the desired trihydrate is insoluble.

* * * * *